United States Patent
Kokelmann (10) Patent No.: US 9,802,036 B2
(45) Date of Patent: Oct. 31, 2017

(54) DEVICE FOR CONTACTING AND ELECTRICALLY STIMULATING BIOLOGICAL TISSUE

(71) Applicant: Retina Implant AG, Reutlingen (DE)

(72) Inventor: Martin Kokelmann, Neckartenzlingen (DE)

(73) Assignee: RETINA IMPLANT AG, Reutlingen (DE)

( * ) Notice: Subject to any disclaimer, the term of this patent is extended or adjusted under 35 U.S.C. 154(b) by 0 days.

(21) Appl. No.: 14/792,770

(22) Filed: Jul. 7, 2015

(65) Prior Publication Data
US 2015/0306379 A1    Oct. 29, 2015

Related U.S. Application Data

(63) Continuation of application No. PCT/EP2013/076096, filed on Dec. 10, 2013.

(30) Foreign Application Priority Data

Jan. 11, 2013 (DE) ........................ 10 2013 100 256

(51) Int. Cl.
*A61N 1/05* (2006.01)
*A61N 1/375* (2006.01)
(Continued)

(52) U.S. Cl.
CPC .............. *A61N 1/0543* (2013.01); *A61N 1/08* (2013.01); *A61N 1/36125* (2013.01); *A61N 1/3758* (2013.01)

(58) Field of Classification Search
CPC ........ A61B 2562/02; A61B 2562/0209; A61B 5/7282; A61B 2018/00839; A61B 5/0017;
(Continued)

(56) References Cited

U.S. PATENT DOCUMENTS 7,257,446 B2 * 8/2007 Greenberg ........... A61N 1/0543
607/54
2002/0196573 A1 12/2002 Nisch et al.
(Continued)

FOREIGN PATENT DOCUMENTS

DE    102006021258    10/2007
DE    102009015389 A    9/2010
(Continued)

OTHER PUBLICATIONS

International Search Report (Including Translation) for corresponding International Application No. PCT/EP2013/076096, dated Feb. 24, 2014.
(Continued)

*Primary Examiner* — Deborah Malamud
(74) *Attorney, Agent, or Firm* — Jason H. Vick; Sheridan Ross PC (57) ABSTRACT

A device for contacting and/or electrically stimulating biological tissue by means of at least one electrode has at least a first unit, on which the at least one electrode is provided and which is configured for implantation in a human or animal body, a second unit, for supplying the first unit with electrical energy, and at least a first and a second conductive track for the voltage supply of the first unit. The first and second conductive tracks are respectively electrically connected to the first and second units and are at different voltage potentials. Spatially between the first and second conductive tracks, at least a first additional conductive track is arranged that is functionally not involved in the voltage supply of the first unit.

24 Claims, 8 Drawing Sheets

(51) Int. Cl.
*A61N 1/08* (2006.01)
*A61N 1/36* (2006.01)

(58) Field of Classification Search
CPC ............... A61B 5/0031; A61B 5/6821; A61B 2562/0233; A61B 5/00; A61B 5/686; A61B 5/6867; A61B 5/076; A61B 5/486; A61B 5/0002; A61B 5/4836; A61N 1/05; A61N 1/04; A61N 1/0472; A61N 1/36; A61N 1/36046; A61N 5/0622; A61N 5/1002; A61N 1/0543; A61N 1/08; A61N 1/36125; A61N 1/37282; A61N 1/375; A61N 1/3758; A61N 2005/0626; A61N 5/0601; G06F 19/3418; G06Q 50/22
See application file for complete search history.

(56) References Cited

U.S. PATENT DOCUMENTS

| | | |
|---|---|---|
| 2003/0114899 A1 | 6/2003 | Woods et al. |
| 2006/0069416 A1 | 3/2006 | Nisch et al. |
| 2006/0173511 A1 | 8/2006 | Greenberg et al. |
| 2007/0142877 A1 | 6/2007 | McLean |
| 2007/0207569 A1 | 9/2007 | Greenberg et al. |
| 2009/0216295 A1 | 8/2009 | Zrenner et al. |
| 2009/0222063 A1 | 9/2009 | Rothermel |
| 2010/0106227 A1 | 4/2010 | Min et al. |
| 2011/0034912 A1* | 2/2011 | de Graff ............... H01L 21/00 606/21 |
| 2012/0130302 A1 | 5/2012 | Wrobel et al. |

FOREIGN PATENT DOCUMENTS

| | | |
|---|---|---|
| EP | 2066402 A2 | 6/2009 |
| WO | WO 00/67676 | 11/2000 |
| WO | WO 2004/067088 | 8/2004 |
| WO | WO 2008/037363 | 4/2008 |

OTHER PUBLICATIONS

Written Opinion for corresponding International Application No. PCT/EP2013/076096, dated Feb. 24, 2014.
International Preliminary Report on Patentability for corresponding International Application No. PCT/EP2013/076096, dated Jul. 23, 2015.

* cited by examiner

DEVICE FOR CONTACTING AND ELECTRICALLY STIMULATING BIOLOGICAL TISSUE

RELATED APPLICATION

This is a continuation application of co-pending international patent application PCT/EP2013/076096, filed Dec. 10, 2013 and designating the United States, which was published in German as WO 2014/108266 A1, and claims priority to German patent application DE 10 2013 100 256, filed Jan. 11, 2013, which are incorporated herein by reference.

BACKGROUND OF THE INVENTION

Field of the Invention

The present invention relates to a device for contacting and/or electrostimulation of biological tissue, preferably a retina, by means of at least one electrode, wherein the device has at least a first unit, on which the at least one electrode is provided and which is configured for implantation in a human or animal body, a second unit, which provides a voltage supply for supplying the first unit with electrical energy, and at least a first and a second conductive track for connecting the voltage supply to the first unit, the conductive tracks respectively being electrically connected to the first unit and second unit and being at different voltage potentials.

Related Prior Art

Such devices are widely known from the prior art.

The first unit, configured as an implant, is used for example as a retinal implant for stimulation of nerve cells in the eye, as a cochlear implant for stimulation of the human inner ear, as a neural implant for stimulation or tapping of electrical signals from regions of the brain, or very generally for stimulation or tapping of electrical signals of biological tissue.

The implants must in this case respectively be supplied with electrical energy, to which end they are connected to a supply unit forming a second unit, which is likewise implanted or arranged outside the body. Provided between the two units, there are current-carrying conductive tracks consisting of noble metals such as gold, platinum or titanium, which are protected from bodily fluids by a plastic sleeve.

In the case of some implants, the connection between the first and second units is produced by means of wires in which electrical signals are transported and the electrical potentials of the supply voltage are provided. The wires are coated with a plastic insulator in order to avoid short circuits. Silicone is mostly used for this, so that the wires are not only insulated from one another but at the same time also provided with good mechanical protection. The silicone enclosing the wires has a thickness great enough to ensure sufficient protection even against the wet environment which is detrimental to electronics.

If, however, retinal implants or neural implants are intended to be provided with electrical energy, then the spatial conditions are very much narrower, because for example only little free space is available in the eye for placement of relatively thick cables.

For this reason, flexible connecting bands are used for the supply of retinal implants, which are configured in the manner of a narrow, elongate flexible printed circuit board. The conductive tracks are in this case embedded between two biocompatible plastic layers. Polyimides, Parylene, LCP (liquid crystal polymer) or silicones may be envisaged as materials for the plastic layers.

Such retinal implants are known for example from WO 2004/067088 A1, WO 2008/037363 A2 and DE 10 2006 021 258 A1, to the content of which reference is hereby expressly made.

The known retinal implants are implanted in the subretinal or epiretinal space of the eye, in which case the second unit may be formed on the same flexible substrate as the first unit, as described for example in DE 10 2006 021 258 A1.

The second unit may in this case contain an infrared receiver which converts incident IR light into electrical energy for supplying the first unit.

It is also known to form the first and second units onto two different substrates, to connect these two substrates to one another by means of a flexible connecting band and to implant both into the eye.

In other applications, the second unit is an external unit which is suitably fastened outside the body, for example on the forehead, as is known for example from WO 2008/037363 A2 or DE 10 2006 021 258 A1.

The external second unit and the implanted first unit are then likewise connected to one another by means of a flexible connecting band, which for example likewise extends in the subretinal space.

The external second unit configured as a supply unit may in this case draw electrical energy for the first unit formed as an implant from batteries, receive it via external cables or obtain it from electromagnetic energy, as is known for example in WO 00/67676 A1.

A feature common to the active retinal implants described above is that they have a multiplicity of stimulation electrodes which deliver electrical stimulation signals to retinal cells to be contacted. A multiplicity of pixel elements are furthermore provided, which convert incident light into the stimulation signals. For further details, reference is made to the documents cited above.

The described retinal implants have already proven themselves in medical terms, but their residence time in the eye is however still limited in technical terms because, after a residence time of less than 100 hours, short circuits or line interruptions occur between the two conductive tracks which connect the first and second units to one another for the purpose of the voltage supply, so that the voltage supply of the implant is no longer ensured and it must be explanted, or replaced.

SUMMARY OF THE INVENTION

In view of the above, it is among others one object of the present invention to refine a device of the type mentioned at the outset in a simple way in terms of design so that the maximum residence time in the implanted state is increased.

According to the invention, in the device mentioned at the outset, this and other objects are achieved in that at least one additional conductive track functionally not involved in the supply of the first unit with electrical energy is provided, which is arranged spatially between the first and second conductive tracks.

In the scope of the present invention, an "additional conductive track functionally not involved in the supply of electrical energy" is intended to mean a conductive track which can be configured technically like the functionally active conductive tracks but is not connected either directly to the ground or directly to a voltage potential of a supply voltage. The additional conductive track is therefore without electrical function for the purpose of the voltage supply, but in a way not to be expected it does increase the residence time of the new device in the implanted state.

Specifically, the inventors have studied implants re-explanted after electrical failure, in order to analyse the fault of the short circuit or line interruption. In this case, it has been found that the surrounding bodily fluid causes the plastic layers to swell, so that pores are formed, into which the fluid and ions dissolved in the fluid can penetrate and also reach the conductive tracks.

With electric voltage applied, an electrolytic process can then take place, which leads to destruction of the conductive track material. The use of noble metals can prevent this process only to a limited extent.

On the flexible substrate of the connecting band, the conductive tracks are usually arranged parallel, so that inductive and capacitive coupling takes place between them, which causes a minor leakage current between the conductive tracks. This effect is known as electromigration, and it leads to material erosion on the two conductive tracks.

The problems identified, which lead to the short circuit or line interruption found between the conductive tracks, are thus due on the one hand to swelling of the insulation layers, between which the conductive tracks are arranged, and on the other hand to electromigration which leads to material erosion.

The inventors of the present application have not adopted the approach of reducing this effect by mechanical reinforcement of the substrates or the connection between the upper and lower substrates and/or by wider dimensions of the conductive tracks and by greater distances between the conductive tracks extending parallel, but have so to speak arranged a third conductive track, namely the additional conductive track, between the two existing conductive tracks.

The effect of the additional conductive track between the first and second conductive tracks is not in this case primarily based on an the distance between the first and second conductive tracks being increased by the insertion of the additional conductive track, since the effect measured in tests by the inventors is significantly greater than was achievable by increasing the spacing.

Furthermore, it has been found that the additional conductive track can have a smaller width than the conductive tracks, having for example only 10% to 20% of the width of the conductive tracks, but has the same thickness.

This has the advantage that the width of the connecting band is not increased too greatly by the insertion of the additional conductive track, so that implantation in the eye or the brain is not impeded.

The conductive tracks and additional conductive tracks may have a thickness which lies between 0.1 μm and 20 μm, the conductive tracks having a width which lies between 10 μm and 1 mm.

In first tests, the inventors were able to show that in the case of implants or connecting bands without an additional conductive track, a short circuit was to be observed after a few hundred to at most about 1000 hours in a liquid environment which replicates the physiological conditions of the implanted state. If the additional conductive track is used, on the other hand, then in one case the residence time was increased to more than 2500 hours, while in a second test the measurement was stopped after 4000 hours because no negative effects were found.

So far, the inventors have no verified explanation of this effect, although it has been observed that although the swelling of the insulation layers was not eliminated, the contact between the insulation layers did remain stable for a longer time. Furthermore, the formation of electromagnetic fields between the first conductive track and the second conductive track seems to be limited or modified by the additional conductive track; at least, it has been observed that the effects of electromigration were significantly reduced in tests with an additional conductive track.

Contrary to expectation, an electrically inactive additional conductive track which is arranged between the two conductive tracks leads to the residence time of the new device in a physiological environment being significantly improved, without the lateral dimensions of the conductive tracks and of the intermediate space between the two conductive tracks needing to be increased greatly, which in any event would only be possible to a limited extent for the use of retinal implants or neural implants.

The present invention can also be used in devices in which more than two conductive tracks extend between the first and second units, at least one additional conductive track being provided between each two neighbouring conductive tracks. This may, for example, be necessary when supply voltages of different polarity and/or voltage levels are intended to be transmitted.

In the scope of the present invention, a conductive track and additional conductive tracks are intended to mean conductive tracks, such as are used in electronic circuits for connecting the supply voltage, embedded between two generally flexible substrates, generally plastic layers. These conductive tracks are printed onto the substrates or structured on the substrates in another way, for example by sputtering, PVD (physical vapour deposition) or electrolytically. The conductive tracks produced in this way generally have a width of less than 1 mm and a thickness of less than 100 μm (micrometers).

In one embodiment, the additional conductive track is potential-free.

An advantage here is that the additional conductive track does not need to be connected at its two ends, i.e. it extends as a blind conductive track which may float in any desired way.

An advantage of this measure is that it can be implemented very simply in terms of design; an additional conductive track merely has to be arranged between the two conductive tracks, but does not need to be connected further.

As an alternative, the additional conductive track may have an electrical resistance relative to the first and/or second conductive tracks which is more than 100 kOhm.

This measure is advantageous when floating additional conductive tracks in the device are disturbing.

The additional conductive track may extend between the first and second conductive tracks over at least 50% of their length, preferably over at least 90% of their length, more preferably over at least their entire length.

This measure is advantageous in design terms since, since depending on the respective geometrical situation, the additional conductive tracks may extend between the first and second conductive tracks only over a part or over the entire length.

A second additional conductive track may be provided beside the first conductive track, in such a way that the first conductive track extends between the first and second additional conductive tracks, a third additional conductive track may be provided beside the second conductive track, in such a way that the second conductive track extends between the first and third additional conductive tracks, at least two additional conductive tracks may be connected to one another at their outer ends.

Furthermore, a further additional conductive track may be provided between the first and second conductive tracks, the first and second additional conductive tracks and the further and the third additional conductive tracks may be connected to one another at their outer ends.

The inventors of the present application have recognized that the protective function is increased further by these measures which are simple to implement in design terms.

The connection of the additional conductive tracks to one another may in this case be carried out by means of contact bridges which extend over the conductive tracks, from which they are electrically insulated. Conversely, it is also possible to extend the conductive tracks via bridges or make them end internally in the closed ring or rectangle of additional conductive tracks in connection pads, from which bonded wire connections lead to the first or second unit.

The device may comprise a flexible connecting band which is mechanically connected to the first unit and the second unit and on which the conductive tracks as well as the additional conductive track or the additional conductive tracks are arranged.

The second unit may then be either spatially separated in the eye or brain or alternatively lie outside the body, as is known from the documents mentioned at the outset. If the first unit and the second unit are formed on a common flexible substrate, however, the conductive tracks extend on this single substrate, the protective effect according to the invention then being achieved when the conductive tracks are formed on a section of the common substrate which acts as a connecting band according to the invention and comprises the additional conductive tracks, since without the additional conductive tracks provided according to the invention, only a limited lifetime of the devices in the implanted state is available.

In one embodiment, the conductive tracks and the additional conductive track or the additional conductive tracks extend parallel to one another, which offers the advantage that the connecting band can be made very narrow, so that it has the advantage for use in retinal implants of requiring little space in the eye, particularly in the subretinal space.

The first conductive track may be connected to ground and the second conductive track may be connected to DC voltage of the supply voltage. The invention may, however, also be used with other supply lines having high potential differences, for example with a supply voltage for which the first conductive track is at −5 volts and the second conductive track is at +5 volts.

In particular when the two conductive tracks extending parallel to one another are at ground and voltage potential, respectively, according to the finding by the inventors rapid occurrence of electromigration takes place, particularly when the conductive tracks extend parallel to one another over longer distances.

In this critical design, the effect according to the invention of the additional conductive track acts particularly advantageously.

In general, the connecting band may have a lower electrically insulating material layer, on which the conductive tracks and the additional conductive track or the additional conductive tracks are fitted, and an upper electrically insulating material layer provided above the conductive tracks and the additional conductive track or the additional conductive tracks, the insulating material layers preferably being made of polyimide.

An advantage here is that, with polyimide, a particularly biocompatible material is used as the insulation layer, the insulating material layers also having sufficient flexibility so that the connecting band can be placed in the eye or out of the eye.

In one particular embodiment, the first unit is a stimulation unit for the retina, which comprises a multiplicity of pixel elements that convert incident light into electrical signals that are emitted via stimulation electrodes.

As already mentioned at the outset, the use according to the invention of additional conductive tracks is advantageous particularly in retinal implants, because for these very narrow spatial specifications are to be taken into account, so that mechanical protection measures can be implemented only with problems.

The second unit is in this case either an implantable supply unit which converts the incident radiation energy into electrical energy for supplying the stimulation unit, as is known from WO 2004/067088 A1 which was mentioned at the outset, or an external supply unit which provides electrical energy for supplying the stimulation unit, as is known for example from DE 10 2006 021 258 A1 or WO 2000/67676 A1 which were mentioned at the outset.

Other advantages may be found in the description and the appended drawing.

It is to be understood that the features mentioned above and those yet to be explained below may be used not only in the combination respectively indicated, but also in other combinations or individually, without departing from the scope of the present invention.

BRIEF DESCRIPTION OF THE DRAWINGS

Embodiments of the invention are represented in the drawing and will be described in more detail in the description below.

DESCRIPTION OF PREFERRED EMBODIMENTS

Figure 1:
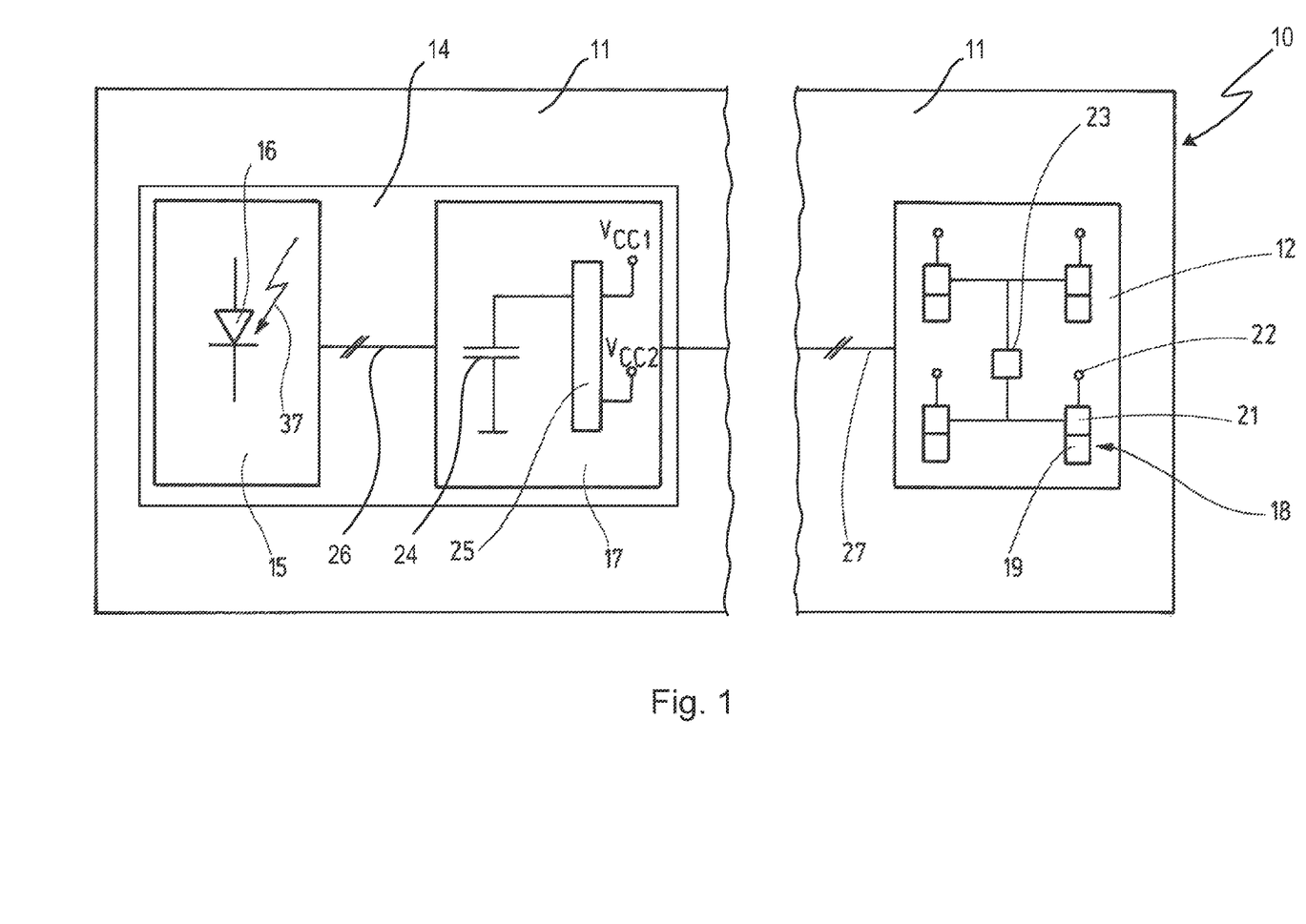
FIG. 1 shows a schematic representation of a fully implantable device for the electrostimulation of the retina, in a representation which is not true to scale.

FIG. 1 schematically represents a device 10 for electrostimulation of the retina, the dimensions not being depicted true to scale.

The device 10 is formed on a substrate in the form of a flexible film 11, on which a stimulation unit 12 and a supply unit 14 are arranged. The supply unit 14 comprises an IR receiver 15 that contains one or more photovoltaic elements 16, which convert incident IR light into electric voltage. The external energy coupled in in this way is transferred to a voltage generator 17, which generates a supply voltage for the stimulation unit 12.

The stimulation unit 12 comprises pixel elements 18, arranged for example in rows and columns, of which only four are represented in FIG. 1 for the sake of clarity. Each pixel element 18 comprises a logarithmic image cell 19 for local image brightness as well as an amplifier 21, which is connected at its output to a stimulation electrode 22. Also provided on the stimulation unit 12, there is an image cell 23 for global brightness, which is connected to the amplifiers 21 of all the pixel elements 18 on the stimulation unit 12. It is to be understood that the stimulation unit 12 may comprise a plurality of global image cells 23, or alternatively only a few thereof.

The voltage generator 17 has a storage element 24, in which the external energy received by the IR receiver 15 is stored. The storage element 24 is connected to a circuit part 25 which, for example, generates two different supply voltages Vcc1 and Vcc2 from the output signals of the IR receiver which are received via a multiple line 26. The supply unit 14 is connected to the sensor unit 12 by means of a plurality of conductive tracks 27. For further details of this device, reference is made to DE 10 2006 021 258 A1 which was mentioned at the outset.

It can be seen from FIG. 1 that the stimulation unit 12 and the supply unit 14 are arranged on the common film 11 as spatially separated units, which are connected to one another by means of the conductive tracks 27. As an alternative, the stimulation unit 12 and the supply unit 14 may also be formed mechanically separately on their own substrates and mechanically connected to one another by means of a connecting band, on which the conductive tracks 27 for supplying the stimulation unit 12 with electrical energy extend.

Figure 3:
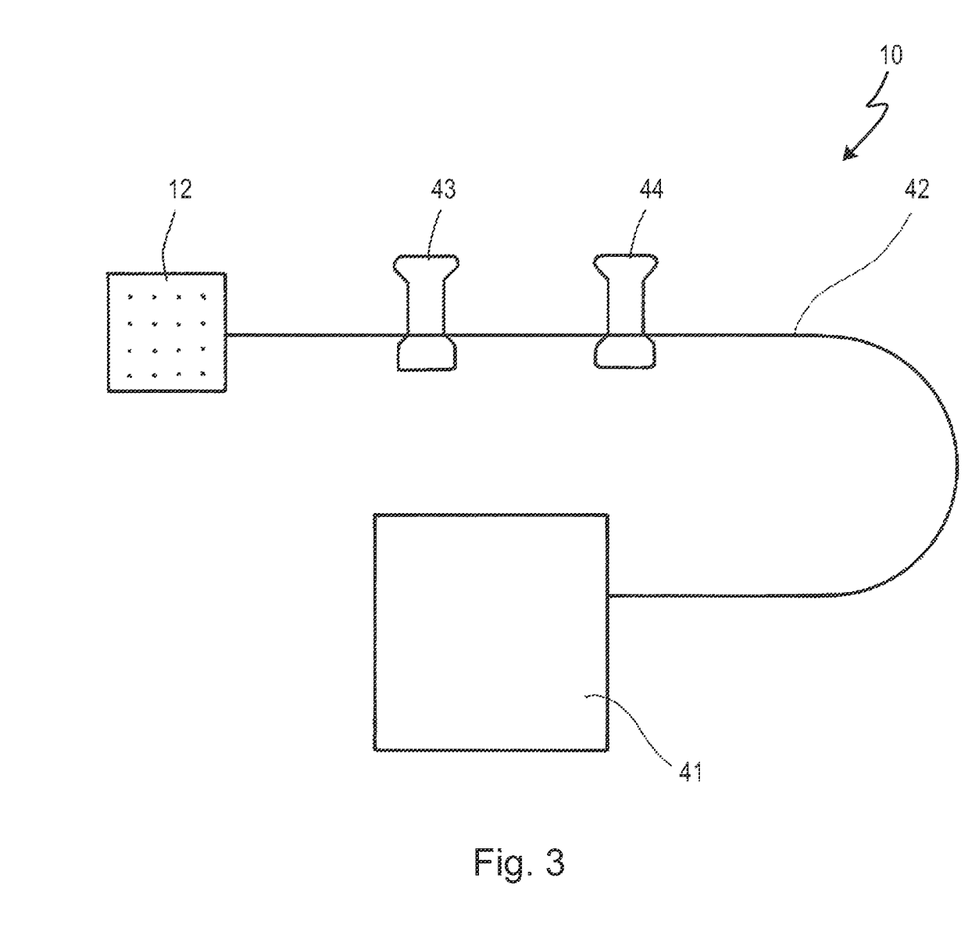
FIG. 3 shows a further device, represented not true to scale, for electrostimulation of the retina, having an implantable stimulation unit and an external supply unit.

The supply unit 14 may in this case likewise be implanted in the eye, as provided in the case of the device 10 of FIG. 1, or it may be arranged outside the eye, as provided in the case of the device 10 of FIG. 3.

Figure 2:
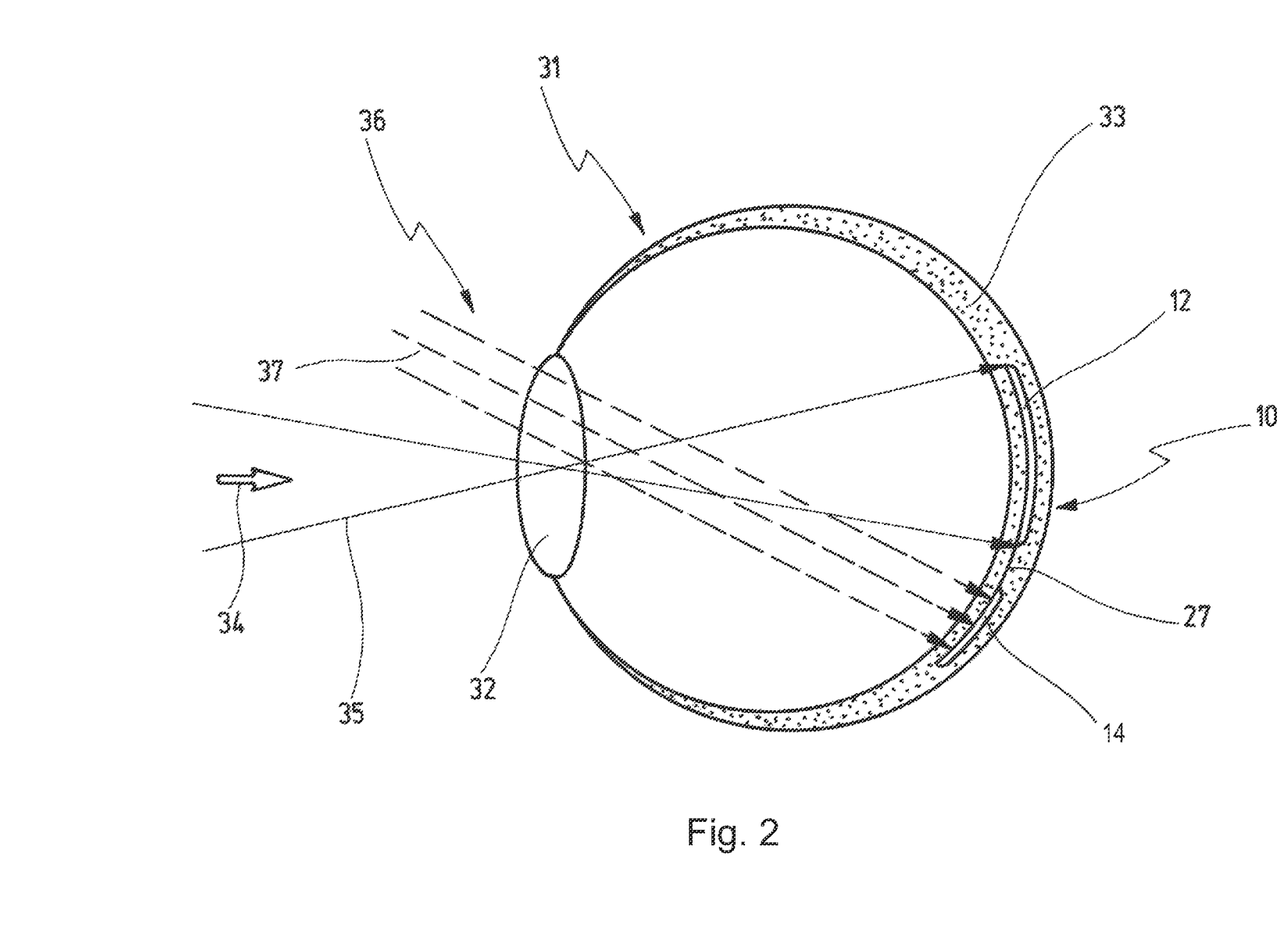
FIG. 2 shows a schematic representation of a human eye into which the device according to FIG. 1 is inserted, likewise not true to scale.

The device 10 of FIG. 1 is intended to be fully implanted into a human eye 31, which is represented very schematically in FIG. 2. For the sake of simplicity, only the lens 32 and the retina 33, into which the device 10 has been implanted, are shown. The device 10 is in this case introduced into the so-called subretinal space, which is formed between the pigment epithelium and the photoreceptor layer. If the photoreceptor layer is degenerated or lost, the subretinal space is formed between the pigment epithelium and the layer of the bipolar and horizontal cells. The device 10 is in this case placed in such a way that stimulation signals can be exerted on cells in the retina 33 by means of the stimulation electrodes 22 shown in FIG. 1.

Visible light 34 indicated by an arrow, the beam path of which is shown at 35, is guided by means of the lens 32 onto the stimulation unit 12, where the visible light 34 is converted into electrical signals that are converted into stimulation signals by means of the amplifiers 21 of FIG. 1.

It can be seen from FIG. 2 that the supply unit 14 lies outside the incidence region of the visible light 34. External energy 36 in the form of rays of IR light 37 are directed onto the supply unit 14 and is converted in the IR receiver 15 into electric voltage that, via the multiple line 26, reaches the voltage generator 17 where corresponding supply voltages are generated from it. The supply voltages then travel via the conductive tracks 27 to the stimulation unit 12, where they are used in order to supply components which convert the incident visible light 34 into stimulation signals.

FIG. 3 shows a further device 10 for electrostimulation of the eye, in a representation which is not true to scale, in which the energy supply takes place not by means of an implanted supply unit 14 that is supplied with energy by IR light coupled in, but by means of an external supply unit 41 which for example is supplied inductively with energy or contains a battery, or is connected in a manner not shown to a battery or a DC voltage source.

The external supply unit 41 is mechanically and electrically connected to a connecting band 42, which is connected at its other end to the stimulation unit 12 already known from FIG. 1. The external supply unit 41 is fastened outside the eye, for example on the patient's head. By means of the supply unit 41, electrical energy is sent to the stimulation unit 12, and at the same time control signals can be transmitted which influence the functionality of the stimulation unit in a manner as described for example in WO 2005/000395 A1, the content of which is hereby made part of the subject matter of the present invention.

Figure 4:
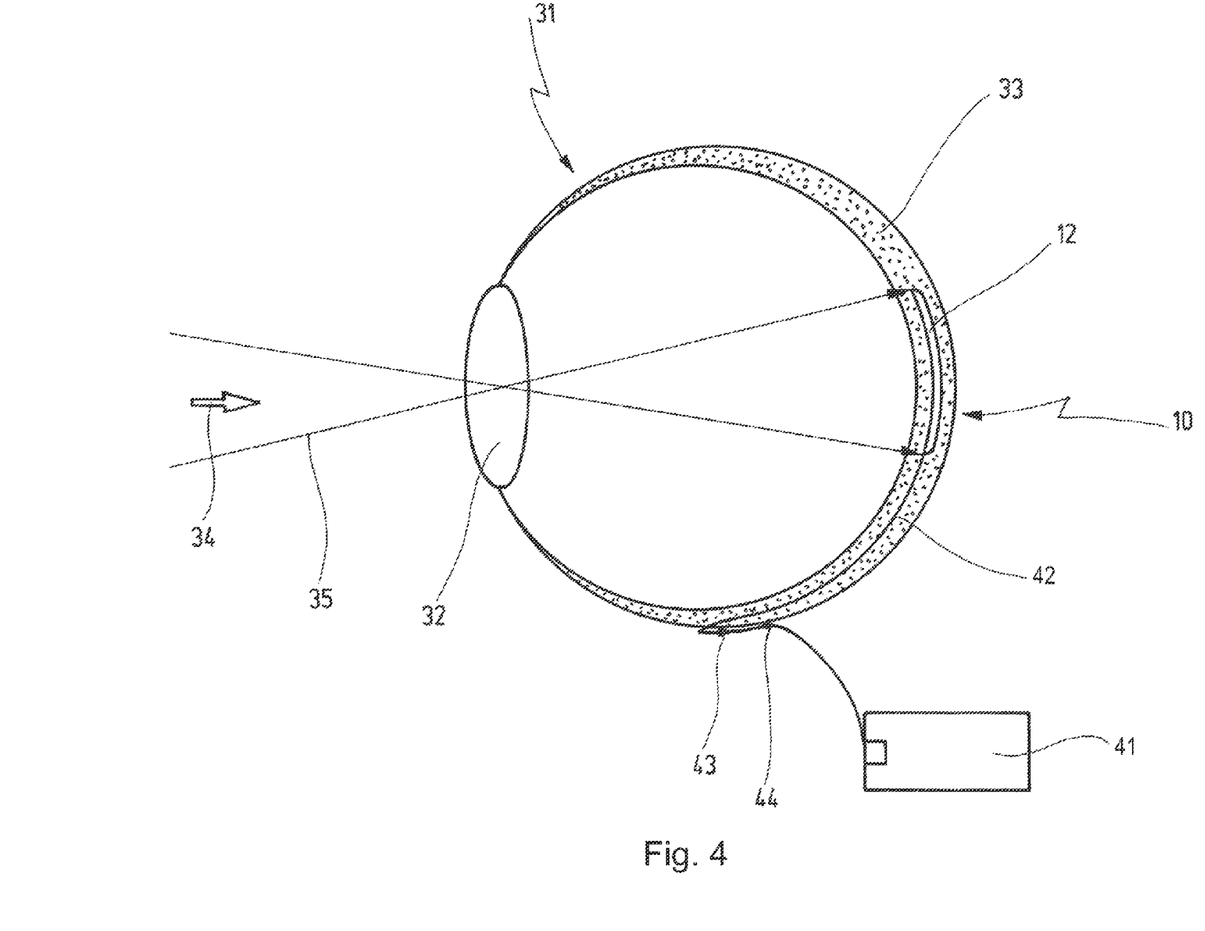
FIG. 4 shows a schematic representation of a human eye as in FIG. 2, but with the device according to FIG. 3.

About 50 mm away from the stimulation unit 12, fastening loops 43 and 44 are provided on the connecting band 42, by means of which the connecting band 42 is fastened immovably on the sclera of the eye, as schematically shown in FIG. 4.

FIG. 4 is a representation like FIG. 2, but this time for the device according to FIG. 3. It can be seen that the connecting band 42 is led out laterally from the eye and is fastened there on the sclera using the fastening loops 43 and 44 before the connecting band 42 continues to the external supply unit 41. This ensures that the stimulation unit 12 is held immovably in the retina 33 in the event of movements of the eye 31.

It should also be mentioned that the dimensions, in particular of the stimulation unit 12, of the fastening loops 43, 44, of the connecting band 42 and of the external supply unit 41 in FIGS. 3 and 4 are represented neither true to scale nor in the accurate size relation to one another.

A connecting band similar to the connecting band 42 may also be used in the device 10 of FIG. 1, in order to connect the stimulation unit 12 and the supply unit 14 to one another. The connecting band 42 may also be formed on the film 11.

In each case, after implantation of the stimulation unit 12, the connecting band 42 lies at least partially in the patient's body, where it comes in contact with bodily fluid, which in the prior art leads even after a short residence time to the problems explained at the outset, i.e. to a short circuit or a conductive track interruption.

Similar problems arise with other devices which are intended for at least partial implantation in the human or animal body for the purpose of contacting and/or electrostimulation of biological tissue.

Such devices also comprise a first unit intended for implantation and a second unit, which is either also implanted or remains outside the body, the two units being formed on a common substrate or on different substrates. Here again, at least two conductive tracks which are connected to the supply voltage and are at different voltage potentials, for example ground or Vcc, extend between the two units.

Figure 5:
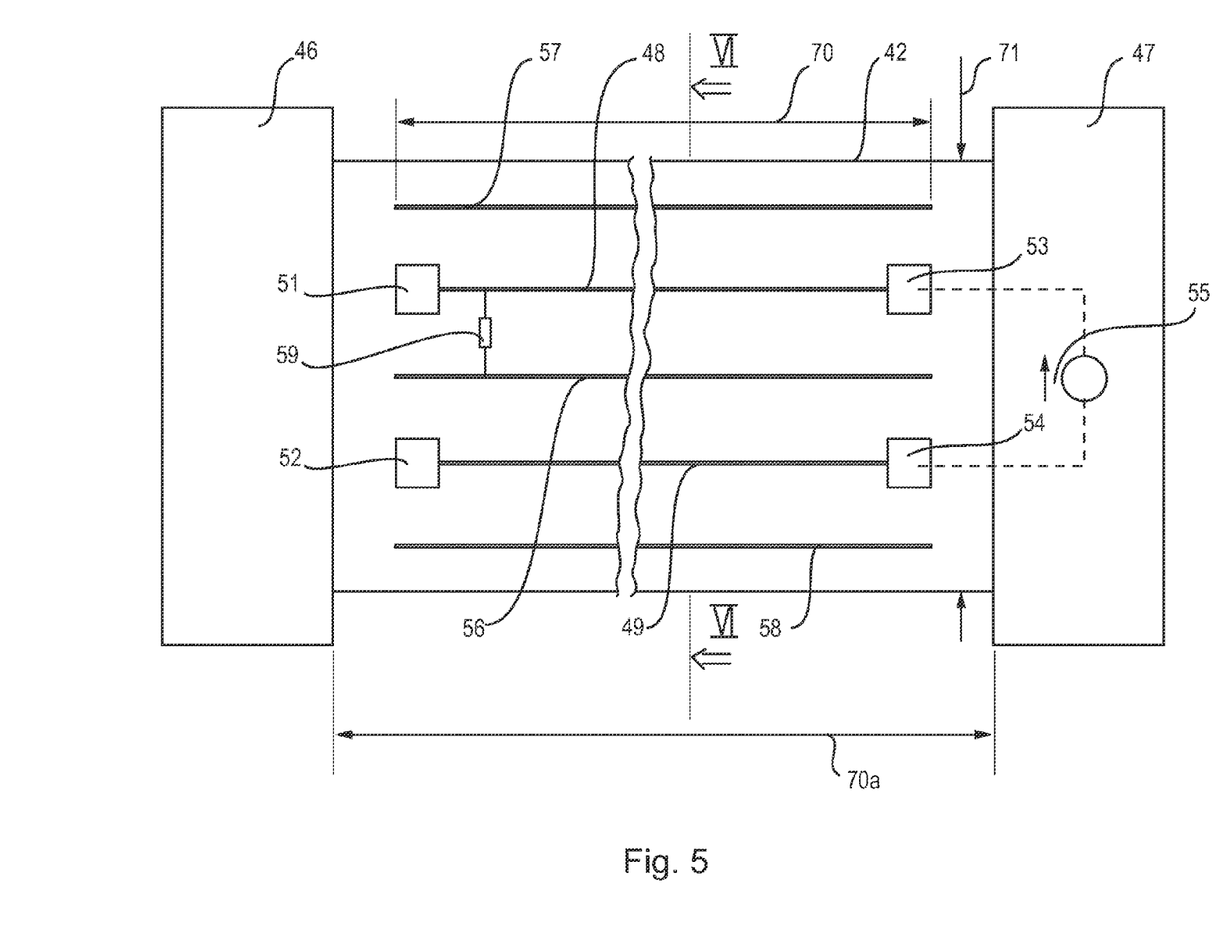
FIG. 5 shows a schematic plan view of a device having an implantable first unit and a second unit, which are connected to one another by means of a connecting band.

FIG. 5 shows in a schematic plan view the connecting band 42 of FIG. 3, the band connecting to one another an implantable first unit 46 and a second unit 47 used for the energy supply of the first unit 46. The two units 46 and 47 are mechanically and electrically connected to the connecting band 42.

Arranged on the connecting band 42, there are two conductive tracks 48, 49, which are connected at their outer ends to connection pads 51, 52, 53 and 54, from which connections (not shown) to the first and second units 46, 47 respectively extend, so that for the purpose of the voltage supply one of the two conductive tracks 48, 49 is at ground potential and the other is at the potential Vcc of the supply DC voltage, which is for example 3 volts. In FIG. 5, 55 indicates a voltage supply, provided for this purpose in the second unit 47, which voltage supply corresponds for example to the voltage generator 17 of the supply unit 14.

Running between the two conductive tracks 48, 49 extending parallel to one another, there is an additional conductive track 56 parallel to the latter, which is not electrically connected either to the first or the second unit 46, 47 or to one of the two conductive tracks 48, 49. The additional conductive track 56 is therefore not involved in the supply of the first unit 46 with energy and consequently to this extent is electrically functionless.

A second additional conductive track 57 extends parallel beside the first conductive track 48, and a third additional conductive track 58 extends parallel beside the second conductive track 49, so that the conductive tracks 48, 49 respectively extend between two additional conductive tracks 56 and 57 or 56 and 58. The second and third additional conductive tracks 57, 58 are also electrically functionless.

For the case in which additional conductive tracks 56, 57, 58 floating in this way are not acceptable for electronic reasons, they may be connected with high impedance to ground, as indicated in FIG. 5, by a resistor 59 which is electrically connected to the conductive track 48 being at ground and the additional conductive track 56 and which has a resistance of 1 megaohm.

The conductive tracks 48, 49 and the additional conductive tracks 56, 57, 58 consist of noble metal, in the present example of printed conductive tracks consisting of gold.

Figure 6:
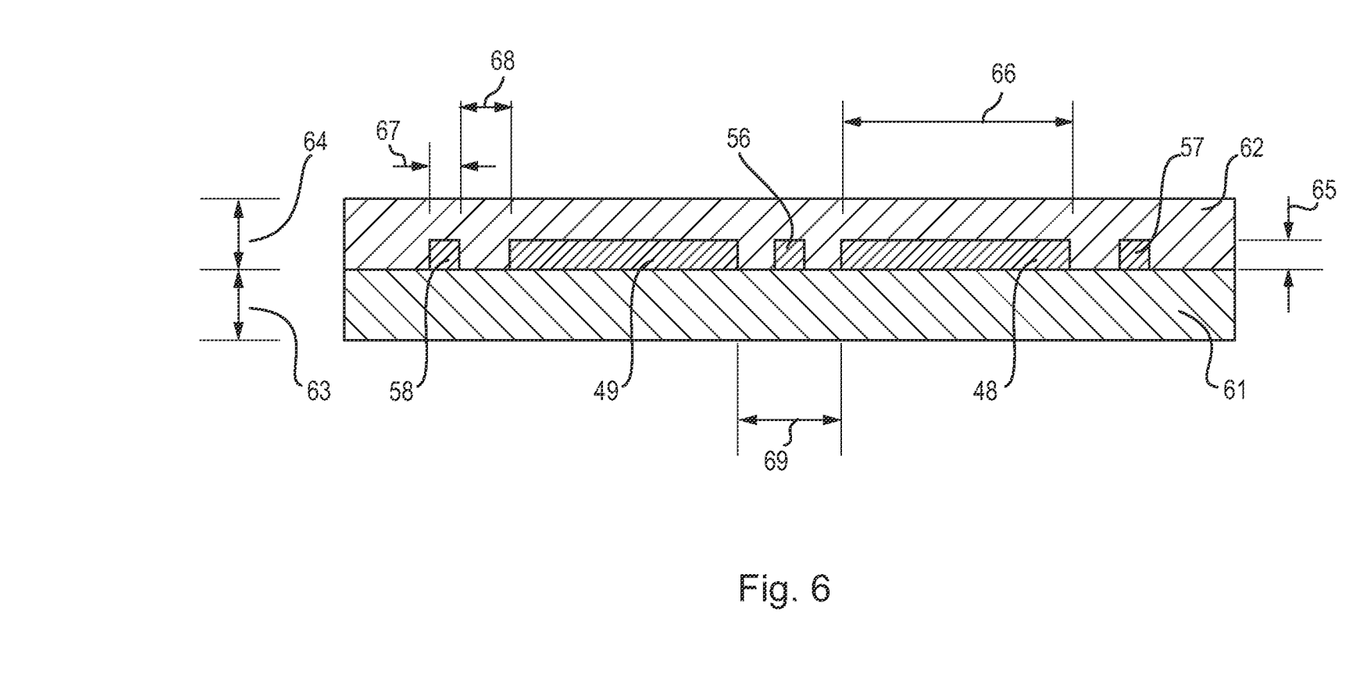
FIG. 6 shows a sectional representation of the device in FIG. 5, seen along line VI-VI of FIG. 5.

FIG. 6 shows a section through the connecting band 42 along the line VI-VI of FIG. 5. The connecting band 42 has a lower insulating material layer 61, arranged on which are the conductive tracks 48, 49 and the additional conductive tracks 56, 57, 58, which are covered by an upper insulating material layer 56. The two material layers 61, 62 consist of polyimide in this example.

The upper material layer 62 fills the intermediate spaces between the conductive tracks 48, 49 and the additional conductive tracks 56, 57, 58, and bears there and outward next to the additional conductive tracks 57 and 58 on the lower material layer 61 and is mechanically connected thereto.

The material layers 61, 62 respectively have a thickness 63, 64 which is about 7 μm (micrometers). The conductive tracks 48, 49 and the additional conductive tracks 56, 57, 58 respectively have a width 65, which is about 3.5 μm. The conductive tracks 48, 49 have a width 66 of respectively 100 μm and the additional conductive tracks 56, 57, 58 respectively have a width 67 of 20 μm, there being a spacing 68 or respectively 69 of 20 μm between the conductive tracks 48, 49 and the intermediate conductive tracks 56, 57, 58.

It can be seen from FIG. 5 that the additional conductive tracks 56, 57, 58 have a length indicated at 70 of 55 mm, which corresponds at least to the length 70a of the conductive tracks 48 and 49 between the connection surfaces 51 and 53, and 52 and 54.

The connecting band 42 in the example of FIG. 5 has a length 70a of about 70 mm and a width 71 of 5 mm.

Without the additional conductive tracks 56, 57, 58, the conductive tracks 48 and 49 would form a short circuit or show a conductive track interruption after a few hundred hours—but not more than about 1000 hours—after implantation in a human or animal body, so that the supply of the first unit 46 with electrical energy is interrupted.

In a way not yet fully clarified, even a high-impedance additional conductive track 56, or one not connected at its two ends, between the two conductive tracks 48 and 49 ensures that the residence time of the connecting band 42 in a physiological environment can be extended significantly. This effect is based not primarily on the distance 69 between the two conductive tracks 48 and 49 having been increased by the insertion of the additional conductive track 56.

Figure 7:
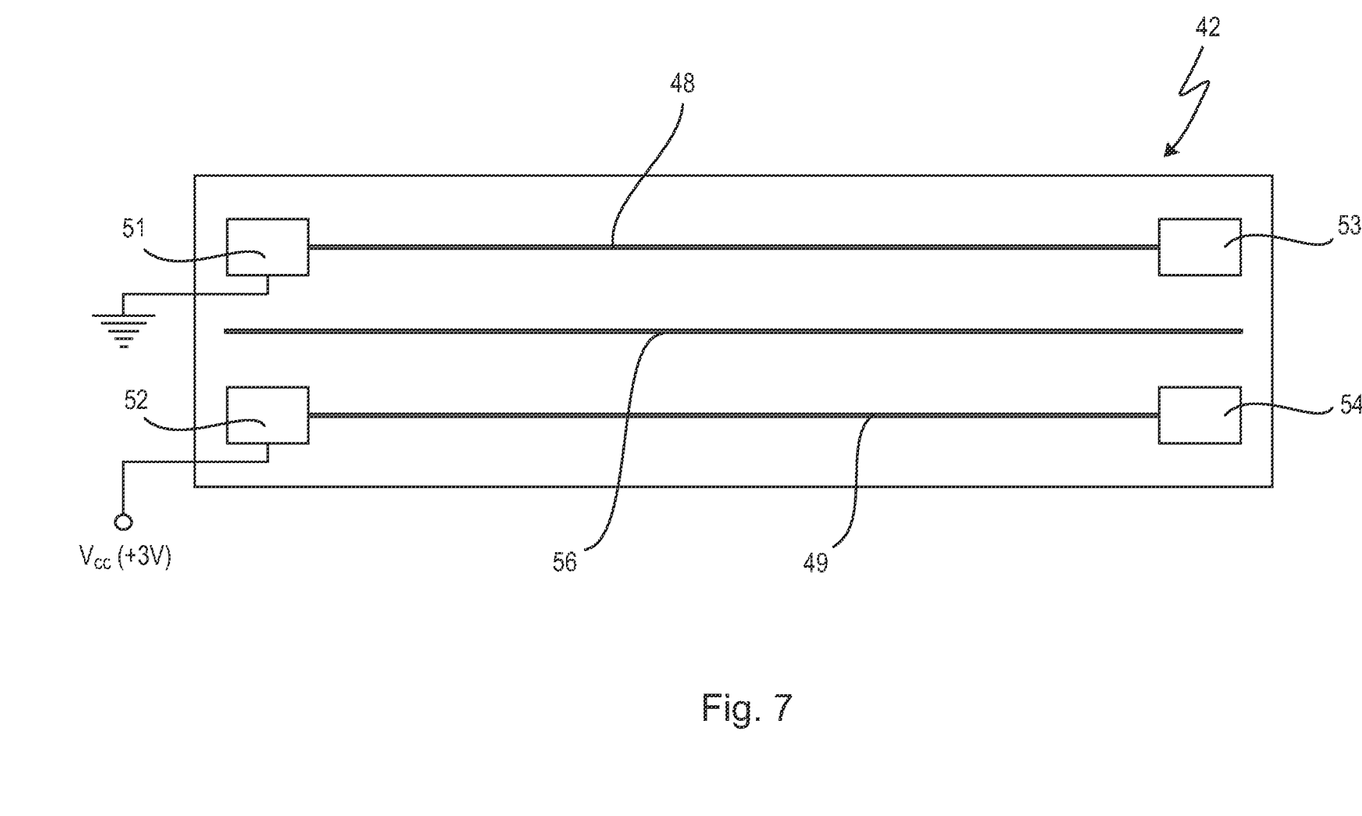
FIG. 7 shows a first embodiment of a connecting band such as may be used for a device of FIGS. 1, 3 and 5, in schematic plan view.

FIG. 7 shows an experimental setup for longterm tests with a connecting band 42, in which the conductive track 48 is grounded on its connection pad 51 and the conductive track 49 is set to the voltage potential of +3 volts on its connection pad 52, and the connecting band 42 is then stored at 37° C. while being fully covered in PBS buffer (phosphate buffered saline: Dulbecco's PBS without calcium and without magnesium).

In a longterm test, the leakage current between the conductive tracks 48, 49 is then measured at the connection pads 53 and 54. In this longterm test, connecting bands 42 with conductive tracks 48, 49 of different widths 66 and different spacings 69 were tested respectively with and without an additional conductive track 56, in order to determine the time until short circuit between the two conductive tracks 48 and 49.

In a first series of tests, no additional conductive tracks 56, 57, 58 were provided, and conductive tracks 48, 49 with widths 66 of 75, 100, 125, 150, 175 and 200 μm (micrometers) were tested, the spacing 69 respectively corresponding to the width 66 of the conductive tracks 48, 49. The time until a short circuit between the conductive tracks 48, 49 was between sometimes less than 100 hours to at most almost 1000 hours, but varied so much for different test objects with a width 66 that no statistically significant correlation could be found between the width 66 and the maximum residence time.

In a second series of tests, an additional conductive track 56 was arranged between the conductive tracks 48, 49, which had a width 67 of 50 μm and a spacing 68 of 75 μm from the neighbouring conductive tracks 48, 49.

These longterm tests were carried out for conductive tracks 48, 49 with a width 68 of 100 μm and 125 μm. The residence time was significantly greater than for the test objects without an additional conductive track, and furthermore the statistical variance turned out to be much less. Residence times of longer than 2500 hours and longer than 4000 hours were measured, before some tests were stopped after a running time of 4000 hours.

This effect can even be induced when the length 70 of the additional conductive track 56 is at least 50% of the length of the conductive tracks 48, 49 between the connection pads 51 and 53, and 52 and 54. When the length 70 is 90% of this length, however, the effect is significantly improved further.

In order to further influence the residence time positively, the conductive tracks 48 and 49 may be enclosed by a second or third additional conductive track 57 or 58, as shown in FIG. 5. The additional conductive tracks 56, 57, 58 may extend with their ends 72, 73, 74, 75, 76, 77 beyond the connection surfaces 51, 52, 53 and 54, and be connected to one another there by transverse tracks 78 and 79, as shown in in FIG. 8.

Figure 9:
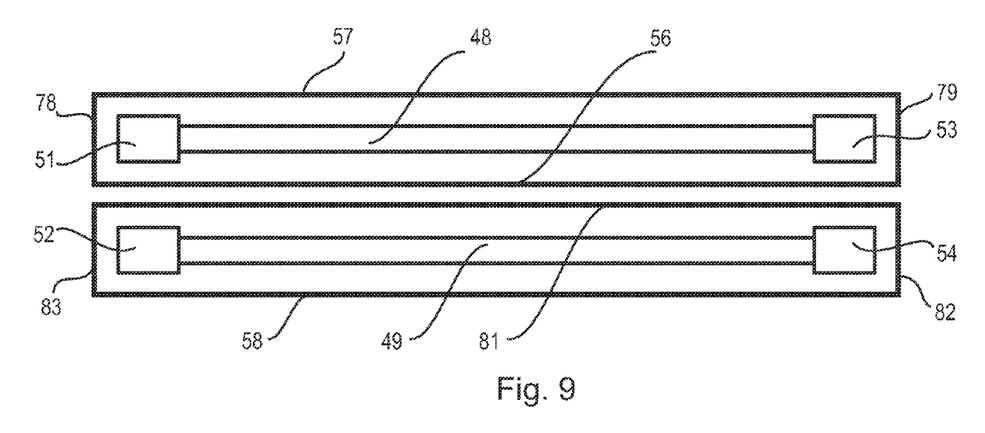
FIG. 9 shows a third embodiment of a connecting band, in a representation as in FIG. 7.

Between the conductive tracks 48 and 49, a further additional conductive track 81 extending parallel to the latter may also be arranged parallel to the additional conductive track 56, in this design as well the additional conductive tracks 56 and 57 being connected to one another by means of transverse tracks 78 and 79 and the additional conductive tracks 81 and 58 being connected to one another by transverse tracks 82 and 83, as shown in FIG. 9.

The transverse tracks 78, 79, 81 have the same width 67 and thickness 65 as the additional conductive tracks 56, 57, 58, 81.

Figure 8:
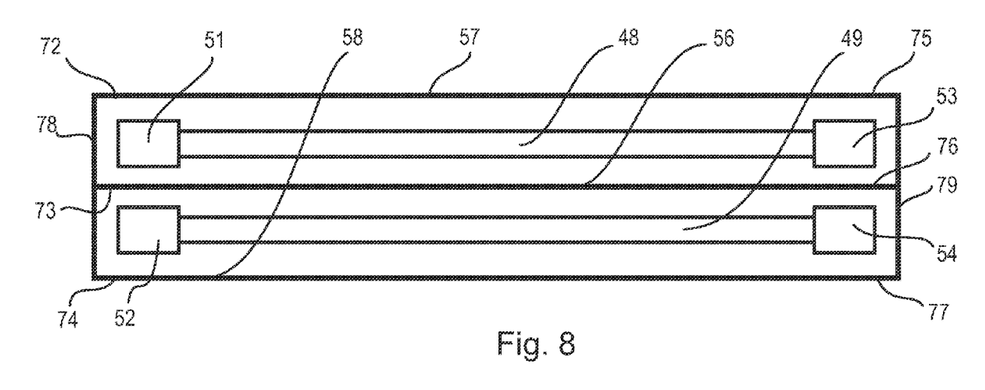
FIG. 8 shows a second embodiment of a connecting band, in a representation as in FIG. 7.

Because the material layers 61, 62 are optically transparent, the conductive tracks 48, 49 and the additional conductive tracks 56, 57, 58, 81 can be seen in the plan views of FIGS. 7 to 9.

Therefore, what is claimed is:

1. A device configured for at least one of contacting and electrically stimulating biological tissue by means of a plurality of electrodes, comprising:
    at least a first unit, the plurality of electrodes being provided on said first unit, said first unit being configured for implantation in a human or animal body, wherein said first unit comprises a stimulation unit configured for a retina and the plurality of said electrodes configured as stimulation electrodes, said stimulation unit comprising a multiplicity of light receiving pixel elements that convert incident light impinging on said pixel elements into electrical signals that are emitted via said stimulation electrodes,
    a second unit that provides a voltage supply for supplying the first unit with electrical energy,
    and at least a first and a second electrical conductor for connecting the voltage supply to said first unit, each electrical conductor being electrically connected to the first unit and to the second unit, said first and second electrical conductors being at different voltage potentials, and said first and second electrical conductors being embedded between two substrates,
    at least a first additional electrical conductor being provided and arranged spatially between the first and second electrical conductor, said first additional electrical conductor being functionally not involved in the supply of the first unit with electrical energy.

2. The device of claim 1, wherein each additional electrical conductor is potential-free.

3. The device of claim 1, wherein each additional electrical conductor has an electrical resistance relative to at least one of the first and second electrical conductors which is more than 100 kohm.

4. The device of claim 1, wherein each electrical conductor extends over a first length, and the first and second electrical conductors extend over a second length, the first length being at least 50% of the second length.

5. The device of claim 4, wherein the first length is at least 90% of the second length.

6. The device of claim 4, wherein the first length is at least as long as the second length.

7. The device of claim 1, wherein a second additional electrical conductor is provided beside the first electrical conductor, such that the first electrical conductor extends between the first and second additional electrical conductors.

8. The device of claim 7, wherein the first and second additional electrical conductors comprise outer ends, said outer ends of said first additional electrical conductor are connected to said ends of said second additional electrical conductor.

9. The device of claim 7, wherein a third additional electrical conductor is provided beside the second electrical conductor and a fourth additional electrical conductor is provided between the first and second electrical conductors, such that the second electrical conductor extends between the fourth and third additional electrical conductors, said first, second, third and fourth additional electrical conductors comprise outer ends, said outer ends of said first additional electrical conductor are connected to said ends of said second additional electrical conductor, and said outer ends of said fourth additional electrical conductor are connected to said ends of said third additional electrical conductor.

10. The device of claim 1, wherein a third additional electrical conductor is provided beside the second electrical conductor, such that the second electrical conductor extends between the first and third additional electrical conductors.

11. The device of claim 10, wherein the first and third additional electrical conductor comprise outer ends, said outer ends of said first additional electrical conductor are connected to said ends of said third additional electrical conductor.

12. The device of claim 1, wherein each additional electrical conductor comprises a first width and each of the first and second electrical conductors comprises a second width, the first width being less than the second width.

13. The device of claim 12, wherein the first width being less than 20% of the second width.

14. The device of claim 13, wherein each of the first and second electrical conductors and each additional electrical conductor has a thickness which lies between 0.1 μm and 20 μm, and wherein each of the first and second electrical conductors has a width which lies between 10 μm and 1 mm.

15. The device of claim 1, wherein each of the first and second electrical conductors and each additional electrical conductor has a thickness (65) which lies between 0.1 μm and 20 μm, and wherein each of the first and second electrical conductors has a width which lies between 10 μm and 1 mm.

16. The device of claim 1, comprising a flexible connecting band mechanically connected to said first unit and said second unit, the first and second electrical conductors and each additional electrical conductor being arranged on said flexible connecting band.

17. The device of claim 16, the flexible connecting band comprising a lower electrically insulating material layer, the first and second electrical conductors and each additional electrical conductor being provided on said lower electrically insulating material layer, and an upper electrically insulating material layer provided above first and second electrical conductors and each additional electrical conductor.

18. The device of claim 17, wherein the upper and lower electrically insulating material layers are made of polyimide.

19. The device of claim 1, wherein the first and second electrical conductors and each additional electrical conductor extend parallel to one another.

20. The device of claim 1, wherein the first electrical conductor is connected to a ground and the second electrical conductor is connected to a DC voltage of said supply voltage.

21. The device of claim 1, wherein said second unit is an implantable supply unit that converts incident radiation energy into electrical energy for supplying said stimulation unit with electric energy.

22. The device of claim 1, wherein said second unit is an external supply unit that provides electrical energy for supplying said stimulation unit with electric energy.

23. A device configured for at least one of contacting and electrically stimulating biological tissue by means of a plurality of electrodes, comprising:
- at least a first unit, the plurality of electrodes being provided on said first unit, said first unit being configured for implantation in a human or animal body, wherein said first unit comprises a stimulation unit configured for a retina and the plurality of said electrodes configured as stimulation electrodes, said stimulation unit comprising a multiplicity of light receiving pixel elements that convert incident light impinging on said pixel elements into electrical signals that are emitted via said stimulation electrodes,
- a second unit that provides a voltage supply for supplying the first unit with electrical energy, and at least a first and a second conductive track for connecting the voltage supply to said first unit, each conductive track being electrically connected to the first unit and to the second unit, said first and second tracks being at different voltage potentials,
- at least a first additional conductive track being provided and arranged spatially between the first and second conductive tracks, said first additional conductive track being functionally not involved in the supply of the first unit with electrical energy,
- and a flexible connecting band mechanically connected to said first unit and said second unit, the first and second conductive tracks and at least said first additional conductive track being arranged on said flexible connecting band.

24. The device of claim 23, wherein each additional conductive track is potential-free.

* * * * *